(12) United States Patent
Angibaud et al.

(10) Patent No.: US 8,506,640 B2
(45) Date of Patent: Aug. 13, 2013

(54) SYSTEMS AND METHODS RELATING TO A KNEE PROSTHESIS CAPABLE OF CONVERSION FROM A CRUCIATE RETAINING TYPE PROSTHESIS TO A POSTERIOR STABILIZNG TYPE PROSTHESIS

(75) Inventors: Laurent Angibaud, Gainesville, FL (US); C. Michael Mauldin, Lake City, FL (US); Scott Gulbransen, Gainesville, FL (US); David Covall, Atlanta, GA (US); Jay Mabrey, Dallas, TX (US); Bernard Stulberg, Chagrin Falls, OH (US)

(73) Assignee: Exactech, Inc., Gainesville, FL (US)

( * ) Notice: Subject to any disclaimer, the term of this patent is extended or adjusted under 35 U.S.C. 154(b) by 541 days.

(21) Appl. No.: 12/558,238

(22) Filed: Sep. 11, 2009

(65) Prior Publication Data
US 2010/0211179 A1  Aug. 19, 2010

Related U.S. Application Data

(60) Provisional application No. 61/096,422, filed on Sep. 12, 2008.

(51) Int. Cl.
*A61F 2/38* (2006.01)
(52) U.S. Cl.
USPC .................. 623/20.27; 623/20.14; 623/20.15; 623/20.28
(58) Field of Classification Search
USPC ................... 623/20.27, 20.14, 20.15, 20.28
See application file for complete search history.

(56) References Cited

U.S. PATENT DOCUMENTS

| | | | |
|---|---|---|---|
| 4,309,778 A | 1/1982 | Buechel et al. | |
| 4,959,071 A * | 9/1990 | Brown et al. | 623/20.27 |
| 5,116,375 A * | 5/1992 | Hofmann | 623/20.27 |
| 5,405,398 A | 4/1995 | Buford, III et al. | |
| 6,168,629 B1 | 1/2001 | Timoteo | |
| 6,264,697 B1 * | 7/2001 | Walker | 623/20.27 |
| 6,558,426 B1 * | 5/2003 | Masini | 623/20.27 |
| 6,582,469 B1 | 6/2003 | Tornier | |
| 6,589,283 B1 * | 7/2003 | Metzger et al. | 623/20.35 |

(Continued)

OTHER PUBLICATIONS

PCT International Search Report based on PCT/US09/056691 mailed on Nov. 6, 2009.

*Primary Examiner* — Thomas J Sweet
*Assistant Examiner* — Seema Mathew
(74) *Attorney, Agent, or Firm* — Greenberg Traurig, LLP

(57) ABSTRACT

One embodiment of the present invention relates to a system in which a knee prosthesis is capable of conversion from a cruciate retaining type prosthesis to a posterior stabilizing type prosthesis. Another embodiment of the present invention relates to a system in which a knee prosthesis is converted from a cruciate retaining type prosthesis to a posterior stabilizing type prosthesis. Another embodiment of the present invention relates to a method in which a knee prosthesis is capable of conversion from a cruciate retaining type prosthesis to a posterior stabilizing type prosthesis. Another embodiment of the present invention relates to a method in which a knee prosthesis is converted from a cruciate retaining type prosthesis to a posterior stabilizing type prosthesis. Another embodiment of the present invention relates to a method of making a knee prosthesis that is capable of conversion from a cruciate retaining type prosthesis to a posterior stabilizing type prosthesis. Another embodiment of the present invention relates to a method of making a knee prosthesis that is converted from a cruciate retaining type prosthesis to a posterior stabilizing type prosthesis.

16 Claims, 11 Drawing Sheets

(56) References Cited

U.S. PATENT DOCUMENTS

| | | |
|---|---|---|
| 6,629,999 B1 | 10/2003 | Serafin, Jr. |
| 7,153,327 B1 | 12/2006 | Metzger |
| 2003/0158606 A1* | 8/2003 | Coon et al. ................ 623/20.15 |
| 2003/0220697 A1* | 11/2003 | Justin et al. ................ 623/20.15 |
| 2004/0102851 A1* | 5/2004 | Saladino ................ 623/20.15 |
| 2004/0243244 A1* | 12/2004 | Otto et al. ................ 623/20.27 |
| 2005/0283252 A1* | 12/2005 | Coon et al. ................ 623/20.35 |
| 2006/0155380 A1* | 7/2006 | Clemow et al. ............ 623/20.35 |
| 2008/0114463 A1 | 5/2008 | Auger et al. |
| 2009/0149964 A1* | 6/2009 | May et al. ................ 623/20.15 |

* cited by examiner

US 8,506,640 B2

SYSTEMS AND METHODS RELATING TO A KNEE PROSTHESIS CAPABLE OF CONVERSION FROM A CRUCIATE RETAINING TYPE PROSTHESIS TO A POSTERIOR STABILIZNG TYPE PROSTHESIS

RELATED APPLICATIONS

This application claims the benefit of U.S. Provisional Application Ser. No. 61/096,422, filed Sep. 12, 2008, which is incorporated herein by reference in its entirety.

FIELD OF THE INVENTION

One embodiment of the present invention relates to a system in which a knee prosthesis is capable of conversion from a cruciate retaining type prosthesis to a posterior stabilizing type prosthesis.

Another embodiment of the present invention relates to a system in which a knee prosthesis is converted from a cruciate retaining type prosthesis to a posterior stabilizing type prosthesis.

Another embodiment of the present invention relates to a method in which a knee prosthesis is capable of conversion from a cruciate retaining type prosthesis to a posterior stabilizing type prosthesis.

Another embodiment of the present invention relates to a method in which a knee prosthesis is converted from a cruciate retaining type prosthesis to a posterior stabilizing type prosthesis.

Another embodiment of the present invention relates to a method of making a knee prosthesis that is capable of conversion from a cruciate retaining type prosthesis to a posterior stabilizing type prosthesis.

Another embodiment of the present invention relates to a method of making a knee prosthesis that is converted from a cruciate retaining type prosthesis to a posterior stabilizing type prosthesis.

BACKGROUND OF THE INVENTION

The debate on whether to keep or sacrifice the posterior cruciate ligament (hereinafter sometimes referred to as "PCL") has existed in the orthopedic community for several years, and is likely to remain for several more. Cruciate retaining (hereinafter sometimes referred to as "CR") knee implants allow for retention of the PCL, while posterior stabilizing (hereinafter sometimes referred to as "PS") knee implants typically feature a mechanism between the femoral component and tibial insert to reproduce femoral rollback and stabilize the knee joint.

Conventional CR and PS designs have their pros and cons. On one hand, CR users typically argue that keeping the PCL helps stability, promotes femoral rollback, and reduces forces transmitted to the bone-implant interface, because the PCL absorbs some of those forces. In addition, CR femoral components typically do not require additional bone cut from the intercondylar area of the femur, making them typically more bone-preservation friendly than PS components. On the other hand, PS users typically argue that removing the PCL helps correct any preexisting deformities, reduces polyethylene (PE) wear, and offers more potential congruency between femoral and tibial components.

It is believed that the knee market (as of 2008) was relatively well balanced between PS and CR knee implants (see FIG. 1—Worldwide knee market segmentation between CR and PS knee implants in 2002 and 2008—2008: 49% PS, 51% CR; 2002: 43% PS, 57% CR).

A CR knee system is typically intended for patients who, in the physician's judgment, have good bone stock and whose ligaments provide adequate mediolateral, anteroposterior, and varus/valgus stability. The PCL is expected to be healthy to help stability and the kinematics of the knee joint (see FIG. 2—Front and back views of the right knee). However, there is a risk the PCL will lose function later and become deficient, which could lead to the need for revision due to instability and pain. In revision cases, the surgeon typically has no other choice than to sacrifice the PCL, remove both the CR femoral component and CR tibial insert, and implant a PS femoral component and PS tibial insert. This type of revision is typically associated with femoral bone loss due to removal of the well-fixed femoral component, and may be particularly harmful to the patient. Because of this risk, some CR-oriented surgeons have been switching to PS implants. The knee market segmentation between CR and PS shown in FIG. 1 illustrates this trend from 2002 to 2008.

Various patents related to prosthetic knees include the following:

U.S. Pat. No. 6,629,999, entitled MODULAR JOINT, which was issued Oct. 7, 2003 in the name of Serafin, Jr.

U.S. Pat. No. 5,405,398, entitled PROSTHETIC KNEE WITH POSTERIOR STABILIZED FEMORAL COMPONENT, which was issued Apr. 11, 1995 in the name of Buford, III, et al.

U.S. Pat. No. 5,116,375, entitled KNEE PROSTHESIS, which was issued May 26, 1992 in the name of Hoffmann.

U.S. Pat. No. 4,309,778, entitled NEW JERSEY MENISCAL BEARING KNEE REPLACEMENT, which was issued Jan. 12, 1982 in the name of Buechel et al.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components (and any size, material and similar details shown in the figures are, of course, intended to be illustrative and not restrictive). Therefore, specific structural and functional details disclosed herein are not to be interpreted as limiting, but merely as a representative basis for teaching one skilled in the art to variously employ the present invention.

Referring now to FIGS. 3, 4, 5, 6A-6B, 7, 8, 9, 10, 11, 12 and 13A-13C, one embodiment of the present invention may provide a CR femoral component that can be converted into a PS femoral component by adding a modular cam during primary or revision surgery if needed (as a result, in revision cases, this embodiment may remove the need to revise the femoral component if the PCL has lost function). This concept of converting the kinematic construct from a CR to a PS is extremely appealing (e.g., this concept should provide great benefits for the user). Various examples of the invention include: (1) a knee prosthesis that can be converted from CR to PS during a primary surgery or during a revision surgery, without the need to remove the tibial baseplate from the patient and without the need to remove the femoral component from the patient; and (2) a method of conversion of a knee prosthesis from CR to PS.

Figure 1:
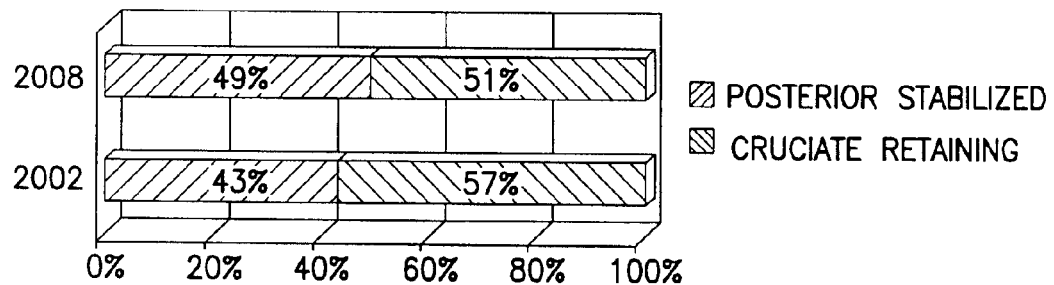
FIG. 1 shows worldwide knee market segmentation between CR and PS knee implants in 2002 and 2008).
Figure 2:
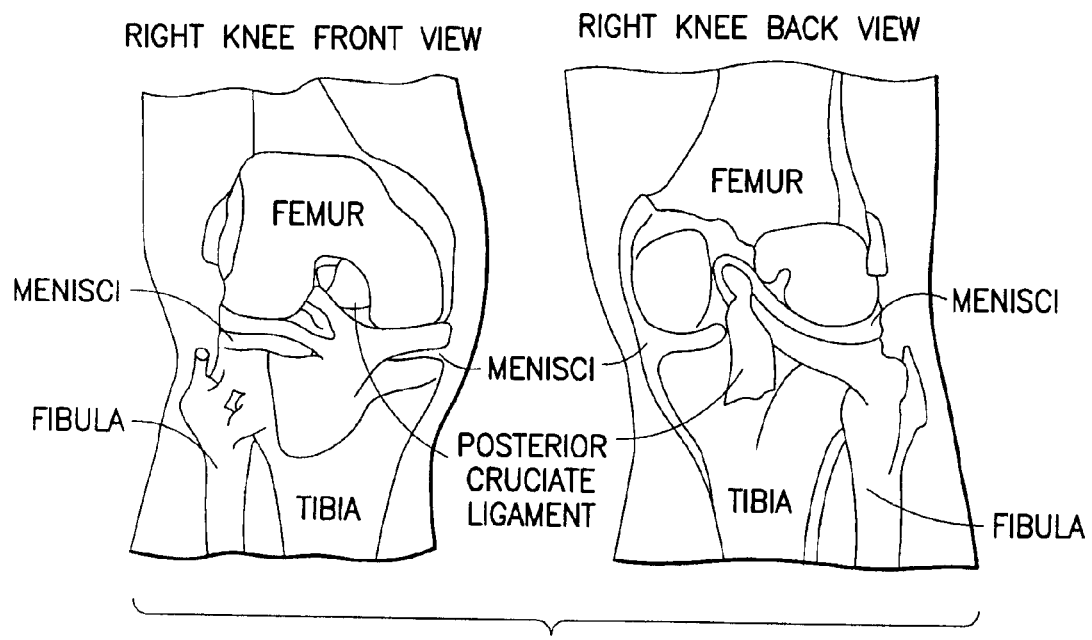
FIG. 2 shows front and back views of the right knee.
Figure 3:
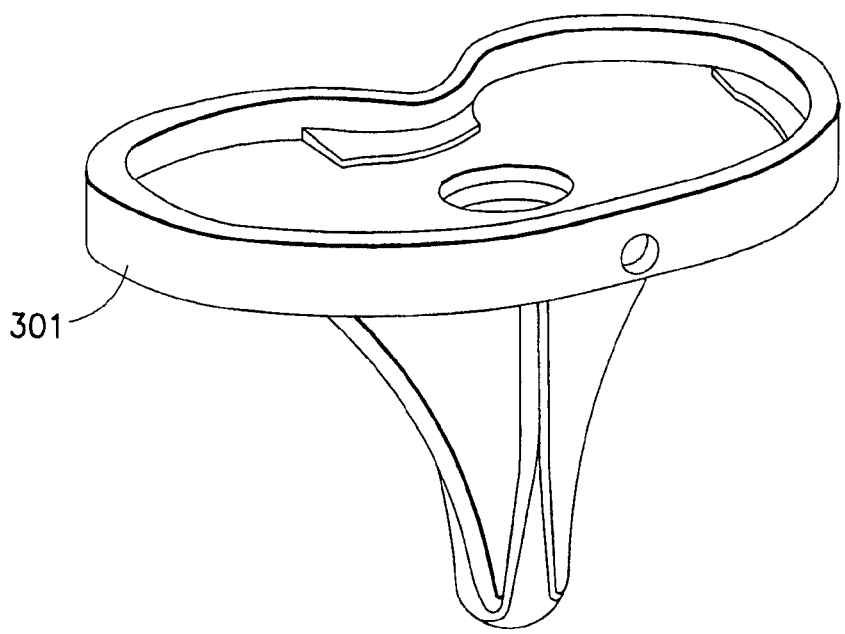
FIGS. 3, 4, 5, 6A, 6B, 7, 8, 9, 10, 11, 12, 13A, 13B and 13C show one embodiment of the present invention (which may provide a CR femoral component that can be converted into a PS femoral component by adding a modular cam during primary or revision surgery if needed).
Figure 4:
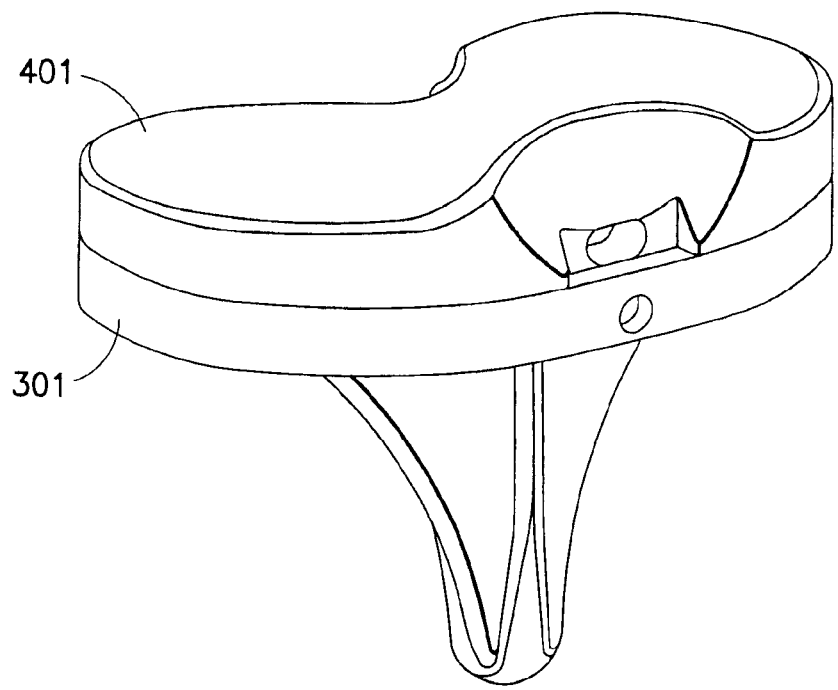
Figure 5:
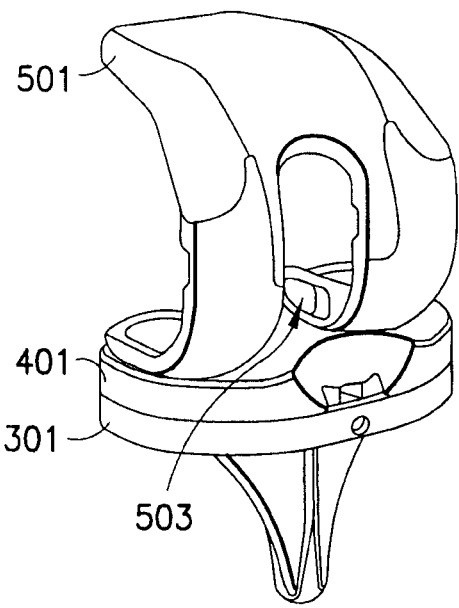
Figure 6A:
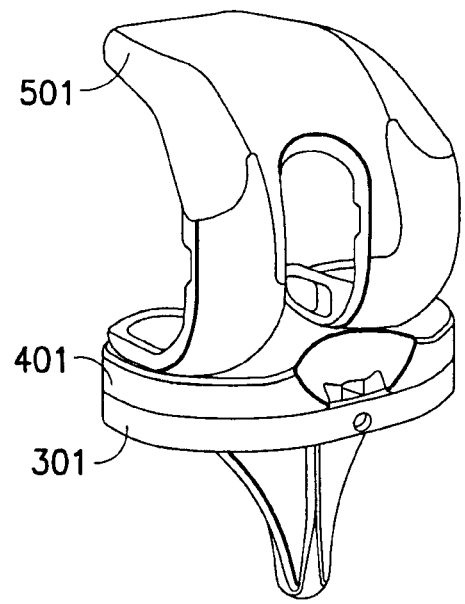
Figure 6B:
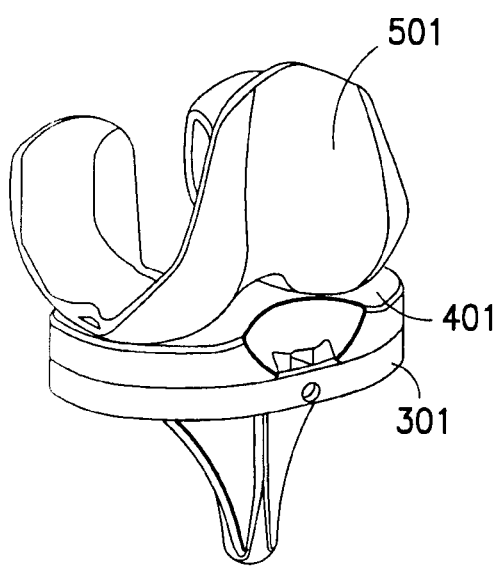
Figure 7:
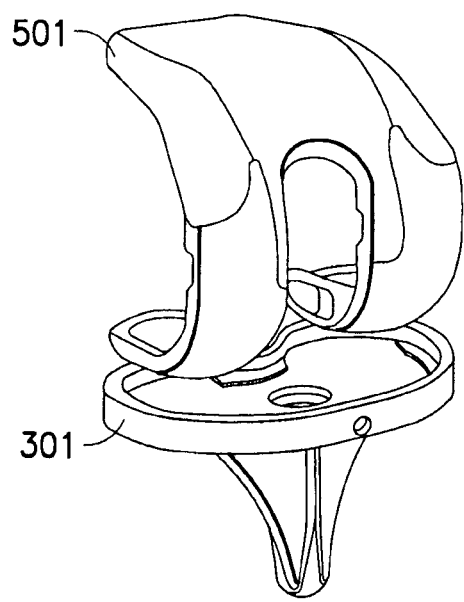
Figure 8:
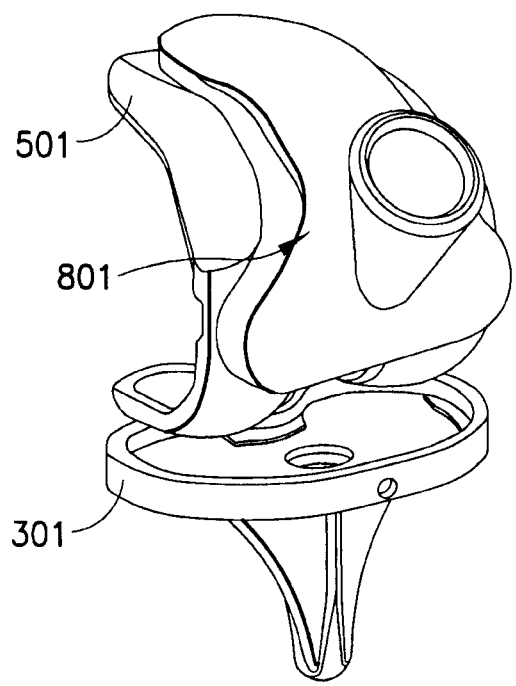
Figure 9:
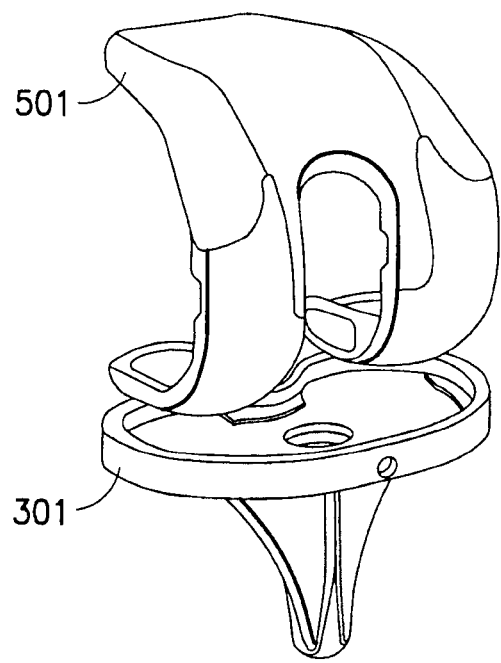
Figure 10:
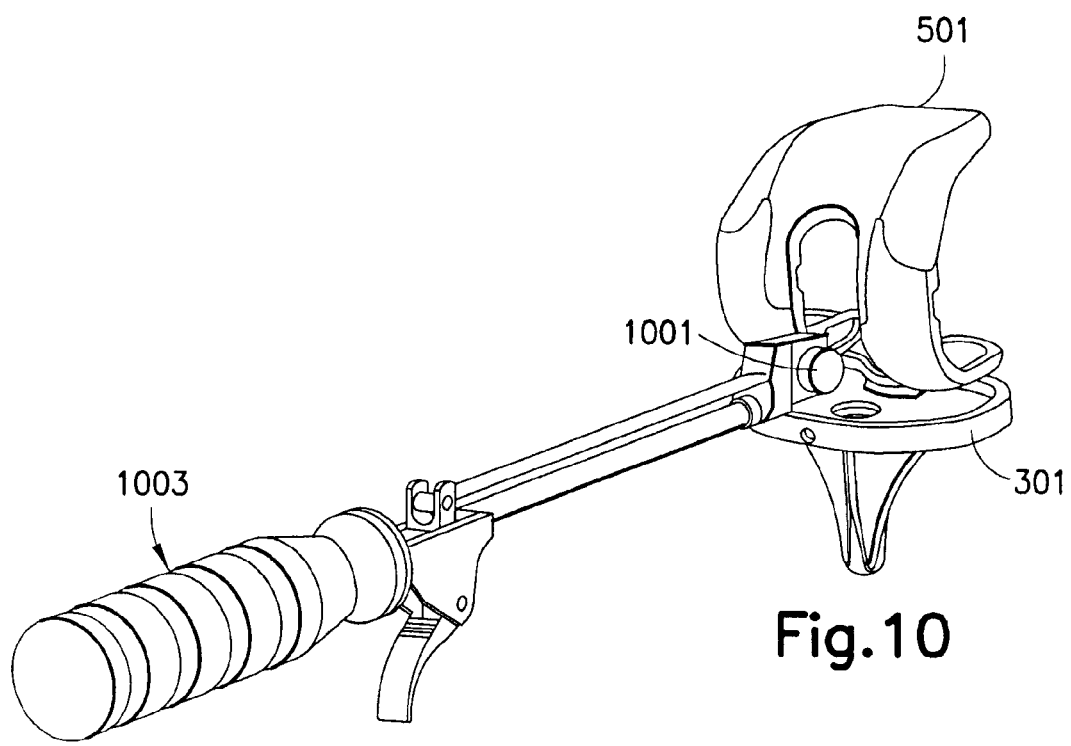
Figure 11:
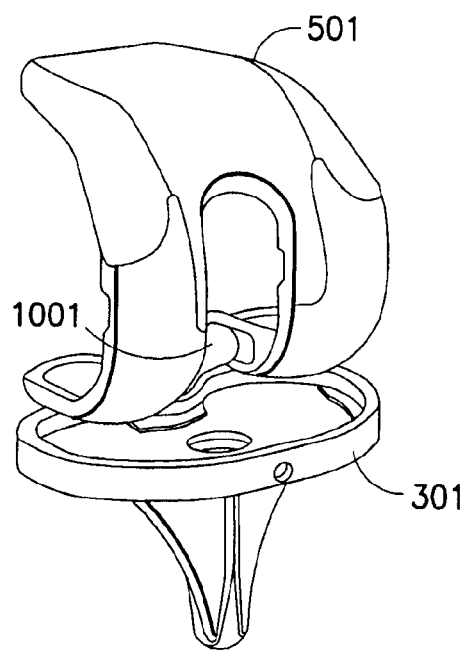
Figure 12:
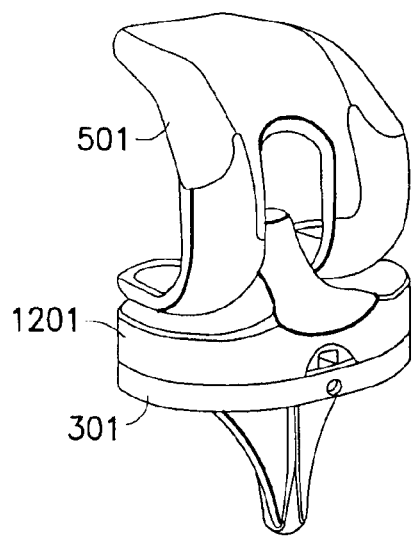

An example of a general sequence of implantation of the knee prosthesis according to an embodiment of the present invention during primary and/or revision surgeries may be as follows:

Operative Technique
During a total knee replacement, the surgeon assesses the patient's posterior cruciate ligament (PCL)
If the PCL functions properly, the surgeon will implant a so-called cruciate retaining (CR) knee system
Implantation of the Tibial Tray (see, FIG. 3)
Placement of the tibial tray prosthesis 301
Implantation of the CR Tibial Insert (see, FIG. 4)
Installation of the CR polyethylene tibial insert 401 into the tibial tray 301
Implantation of the CR Femoral Component (see, FIG. 5)
Placement of the femoral component 501
Note that the locking mechanism protector 503 is in place in order to avoid any bone cement (e.g., if the femoral component is cemented) and/or soft tissue penetration
General View of the CR Components After Implantation (see, FIGS. 6A, 6B)
FIG. 6A shows: CR Femoral 501 at 90 degrees of flexion
FIG. 6B shows: CR Femoral 501 at 0 degrees of flexion
Operative Technique
After implantation of the tibial and femoral components, the PCL could be found deficient, which would likely result in instability of the knee joint and pain.
In this case, the surgeon can utilize the versatility of the functionality of the knee system by converting it from a CR implant into a PS implant
Removal of the CR Tibial Insert (see, FIG. 7)
Intercondylar Box Preparation (see, FIG. 8)
Reaming of the intercondylar box by using a bushing guide 801 directly applied to the implanted femoral component (in one example, a size-specific bushing guide may receive the reamer that will prepare the intercondylar box)
Removal of the Protector (see, FIG. 9)
Removal of the locking mechanism protector 503 from the femoral component 501
Implantation of the Modular Cam (see, FIG. 10)
Align the modular cam 1001 with the femoral locking mechanism (disposed on the femoral component 501) and assemble the modular cam 1001 with the femoral component 501 (using the modular cam impactor 1003)
Implantation of the Modular Cam (see, FIG. 11)
Modular cam 1001 shown here assembled with the femoral component 501
Implantation of the PS Tibial Insert (see, FIG. 12)
Installation of the PS polyethylene tibial insert 1201 into the tibial tray 301
General View of the PS Components (Including PS Polyethylene Tibial Insert 1201 and Femoral Component 501 with Assembled Modular Cam 1001) After Conversion (see, FIGS. 13A-13C)

In other embodiments of the present invention different types of attachment of the modular cam to the femoral component may be provided.

Figure 14A:
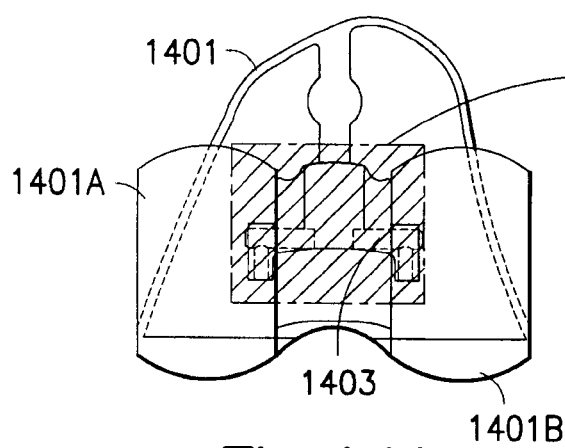
FIGS. 14A and 14B show another embodiment of the present invention (in these FIGS. 14A and 14B, FIG. 14B is a view showing certain detail of a portion of FIG. 14A—in particular, as indicated by the curved arrow pointing from the shaded box area of FIG. 14A (the shaded box area does not, of course, form part of the prosthesis) to FIG. 14B, FIG. 14B shows certain detail of a modular cam element according to an embodiment of the present invention).
Figure 14B:
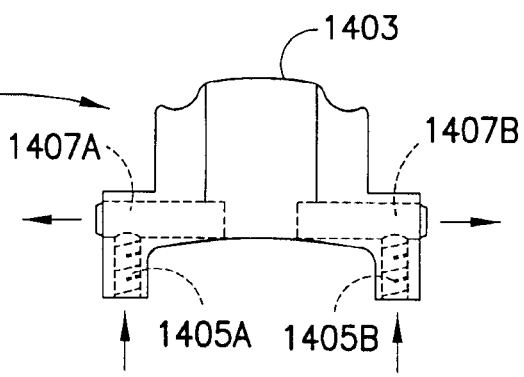

In one example, a modular cam 1403 may be attached to both condyles 1401A,1401B of a femoral component 1401 using, e.g., locking screws 1405A,1405B (see FIGS. 14A and 14B). In this example, turning locking screws 1405A and 1405B at step 1 (such that locking screws 1405A and 1405B move inwards in the direction of the arrows adjacent the locking screws) displaces locking pins 1407A and 1407B at step 2 (such that locking pin 1407A moves outwards, towards the femoral condyle 1401A in the direction of the arrow adjacent the locking pin 1407A and such that such that locking pin 1407B moves outwards, towards the femoral condyle 1401B in the direction of the arrow adjacent the locking pin 1407B). This action thus completes the impaction and locking of the modular cam to the femoral component.

Figure 15A:
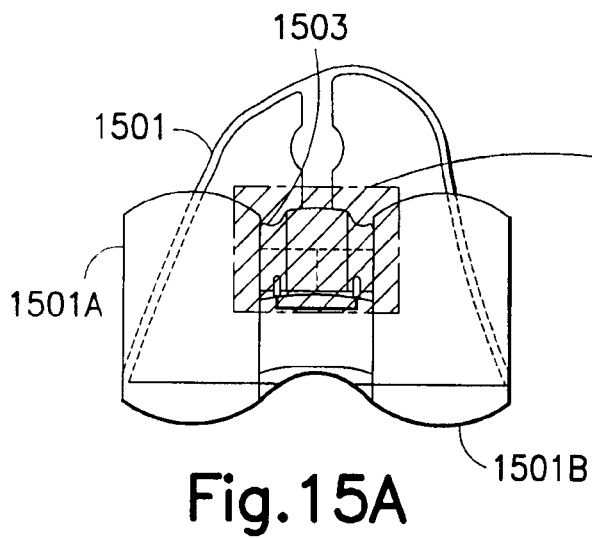
FIGS. 15A, 15B and 15C show another embodiment of the present invention (in these FIGS. 15A, 15B and 15C, FIGS. 15B and 15C are views showing certain detail of a portion of FIG. 15A—in particular, as indicated by the curved arrow pointing from the shaded box area of FIG. 15A (the shaded box area does not, of course, form part of the prosthesis) to FIGS. 15B and 15C, FIGS. 15B and 15C show certain detail of a modular cam element according to an embodiment of the present invention).
Figure 15B:
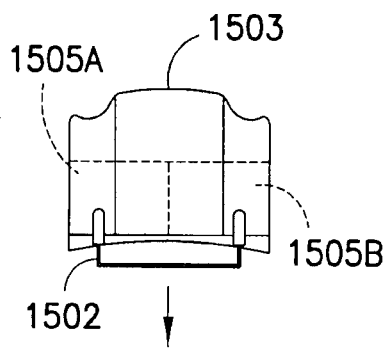
Figure 15C:
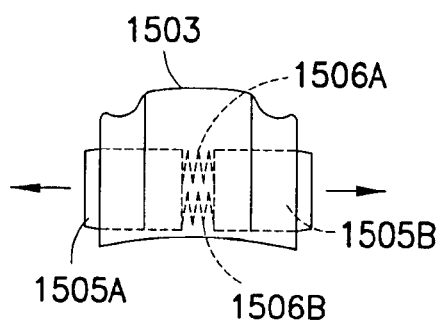

In another example, a modular cam 1503 may be attached to both condyles 1501A,1501B of a femoral component 1501 using, e.g., spring-loaded locking pins 1505A,1505B (see FIGS. 15A, 15B and 15C). In this example, the modular cam may be packaged (e.g., prior to sterilization) such that a holder 1502 (e.g., shaped like a staple or the like) maintains the spring-loaded locking pins 1505A,1505B in position adjacent one another (see FIG. 15B). At the time of surgery, the surgeon need only to remove holder 1502 (see step 1 in FIG. 15B showing the removal of holder 1502 along the direction of the arrow adjacent thereto). Removal of holder 1502 then releases the spring-loaded locking pins 1505A, 1505B (see step 2 of FIG. 15C showing the biasing outward of the spring-loaded locking pin 1505A along the direction of the arrow adjacent thereto and the biasing outward of the spring-loaded locking pin 1505B along the direction of the arrow adjacent thereto). Of course, the removal of the holder 1502 may be done while modular cam 1503 is in place between condyles 1501A,1501B such that the outward biased spring-loaded locking pins 1505A,1505B lock modular cam 1503 in place on the femoral component 1501. In this example, each of the spring-loaded locking pins 1505A, 1505B may be biased outward under the effect of one or more springs (see, e.g., springs 1506A,1506B). In other examples, any desired biasing mechanism(s) may be used.

In another example, a modular cam may be attached to one condyle of the femoral component (see FIGS. 16A-16F, showing modular cam 1603 attached to one condyle 1601A of femoral component 1601—of course, the modular cam may be attached to either condyle, as desired). More particularly, as seen for example in FIGS. 16A and 16B (which show a top view and top cross-section view, respectively) modular cam 1603 may have a portion with a dovetail configuration that slides into and mates with a corresponding dovetail configuration provided on condyle 1601A of femoral component 1601. Further, as seen for example in FIGS. 16C-16F, the following four steps may be used when attaching modular cam 1603 to femoral component 1601: (1) place the modular cam 1603 between the condyles 1601A,16001B; engage the modular cam 1603 inside the tapered dovetail of condyle 1601A; impact the modular cam 1603 along the tapered dovetail of condyle 1601A; and remove the clip(s) holding locking pin 1603A—see FIG. 16B (locking pin 1603A may then be biased outward (e.g., biased by one or more springs or the like) to lock modular cam 1603 to condyle 1601A. In this example, the modular cam is attached to one condyle of the femoral component. In another example, the modular cam may be attached to both condyles of the femoral component (e.g., bridging the two condyles). In another example, the locking pin 1603A may be screwed inward to lock the modular cam 1603 to the condyle 1601A (a through hole to an outer surface of the modular cam may be provided to permit a screw driver or the like to turn the locking pin for this purpose).

In another embodiment of the present invention a prosthesis (e.g., for implantation in a patient) is provided, comprising: a femoral component (see, e.g., femoral component 1601 of FIGS. 16A-16F), wherein the femoral component comprises a first condyle (see, e.g., condyle 1601A of FIGS. 16A-16F) and a second condyle (see, e.g., condyle 1601B of FIGS. 16A-16F), wherein the first condyle and the second condyle are disposed apart from one another such that there is a space between the first condyle and the second condyle, wherein the first condyle comprises at least a first surface generally facing the second condyle across the space between the first condyle and the second condyle (see, e.g., the surface adjacent the mounted modular cam 1603 of FIGS. 16A-16F); a first attachment mechanism (see, e.g., the female portion of the dovetail joint seen in FIG. 16B) associated with the first surface of the first condyle; and a stabilizing mechanism (see, e.g., modular cam 1603 of FIGS. 16A-16F), wherein the stabilizing mechanism comprises a second attachment mechanism (see, e.g., the male portion of the dovetail joint seen in FIG. 16B); wherein the stabilizing mechanism is attached to the first condyle via a mating between the first attachment mechanism associated with the first surface of the first condyle and the second attachment mechanism of the stabilizing mechanism; and wherein the stabilizing mechanism is attached to the first condyle from a position in the space between the first condyle and the second condyle (see, e.g., FIGS. 16A-16F).

In one example, the first condyle may be a left condyle and the second condyle may be a right condyle.

In another example, the first condyle may be a right condyle and the second condyle may be a left condyle.

Figures 16A, 16B:
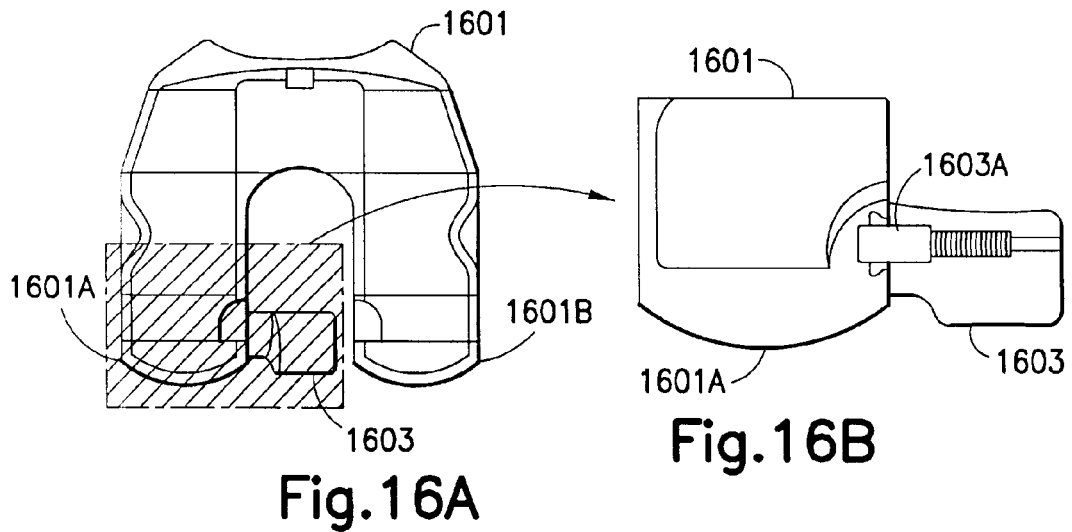
FIGS. 16A-16F show another embodiment of the present invention (of note, FIG. 16B is a view showing certain detail of a portion of FIG. 16A—in particular, as indicated by the curved arrow pointing from the shaded box area of FIG. 16A (the shaded box area does not, of course, form part of the prosthesis) to FIG. 16B, FIG. 16B shows certain detail of a modular cam element according to an embodiment of the present invention; further, FIGS. 16C-16F show four example steps relating to assembly of a modular cam element to a femoral component according to an embodiment of the present invention).
Figures 16C, 16D:
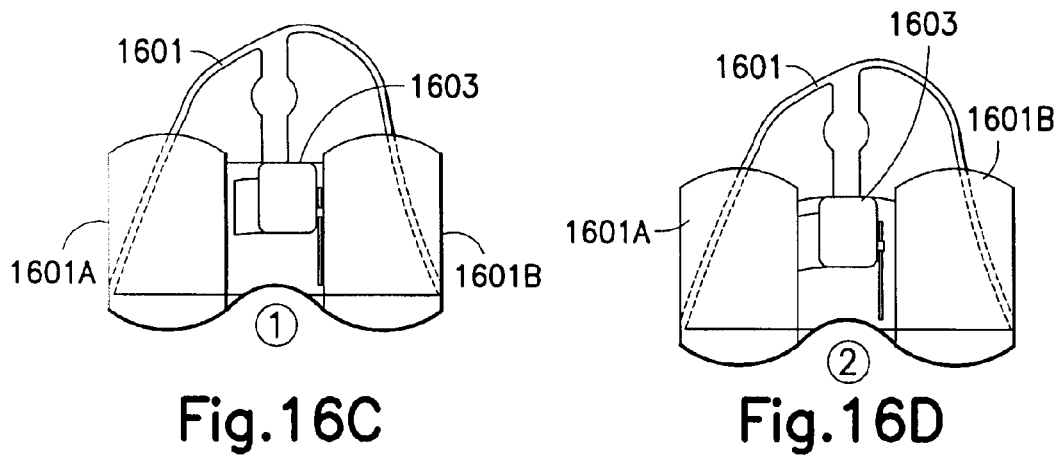
Figures 16E, 16F:
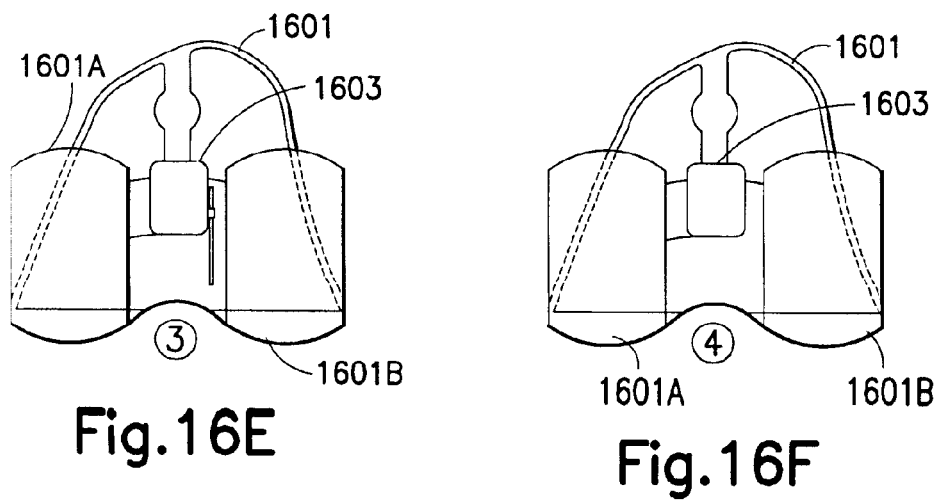

In another example, the first attachment mechanism may comprise a female portion of a dovetail joint (see, e.g., the dovetail joint shown in FIG. 16B).

In another example, the first attachment mechanism may comprise a male portion of a dovetail joint.

In another example, the second attachment mechanism may comprise a female portion of a dovetail joint.

In another example, the second attachment mechanism may comprise a male portion of a dovetail joint (see, e.g., the dovetail joint shown in FIG. 16B).

In another example, the first attachment mechanism may comprise a locking pin and the second attachment mechanism may comprise a hole for receiving the locking pin.

In another example, the locking pin may be biased towards the hole by at least one spring.

In another example, the second attachment mechanism may comprise a locking pin (see, e.g., locking pin 1603A of FIG. 16B) and the first attachment mechanism may comprises a hole for receiving the locking pin (see, e.g., FIG. 16B).

In another example, the locking pin may be biased towards the hole by at least one spring.

In another example, the first attachment mechanism may be on the first surface of the first condyle.

In another example, the first attachment mechanism may be under the first surface of the first condyle.

In another example, the stabilizing mechanism may comprise a cam (see, e.g., modular cam 1603 of FIGS. 16A-16F).

In another example, the stabilizing mechanism may be removably attached to the first condyle.

In another example, the stabilizing mechanism may be essentially permanently attached to the first condyle.

In another example, the stabilizing mechanism may stabilize the femoral component by interfacing with a corresponding feature on a tibial insert adjacent the femoral component (see, e.g., FIGS. 12 and 13A-13C).

In another example, the tibial insert is disposed upon a tibial tray (see, e.g., FIGS. 12 and 13A-13C).

In another example, when the stabilizing mechanism is attached to the first condyle from a position in the space between the first condyle and the second condyle the stabilizing mechanism may be disposed entirely in the space between the first condyle and the second condyle (see, e.g., FIGS. 16A-16F).

In another example, when the stabilizing mechanism is attached to the first condyle from a position in the space between the first condyle and the second condyle the stabilizing mechanism may be disposed at least partially in the space between the first condyle and the second condyle (see, e.g., FIGS. 16A-16F).

Figure 18:
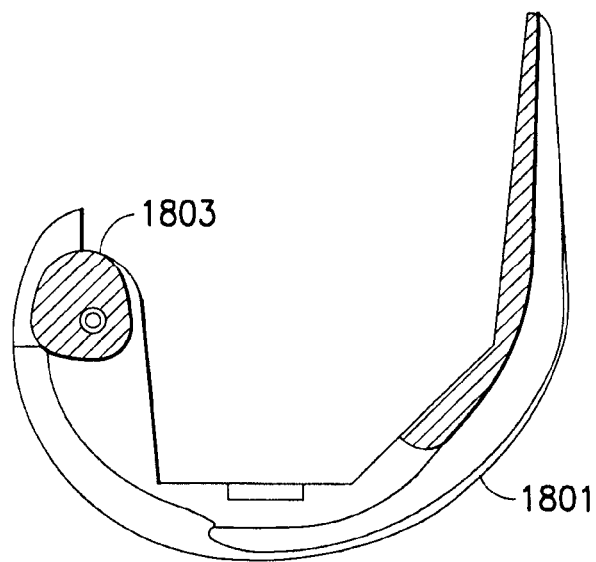
FIG. 18 shows a side cross-section view of a femoral component (and modular cam) according to an embodiment of the present invention.

In another example, the cam may have a cam profile (see, e.g., profile of modular cam 1803 of FIG. 18).

In another example, the cam profile may be in a sagittal plane (see, e.g., profile of modular cam 1803 of FIG. 18).

Figure 19:
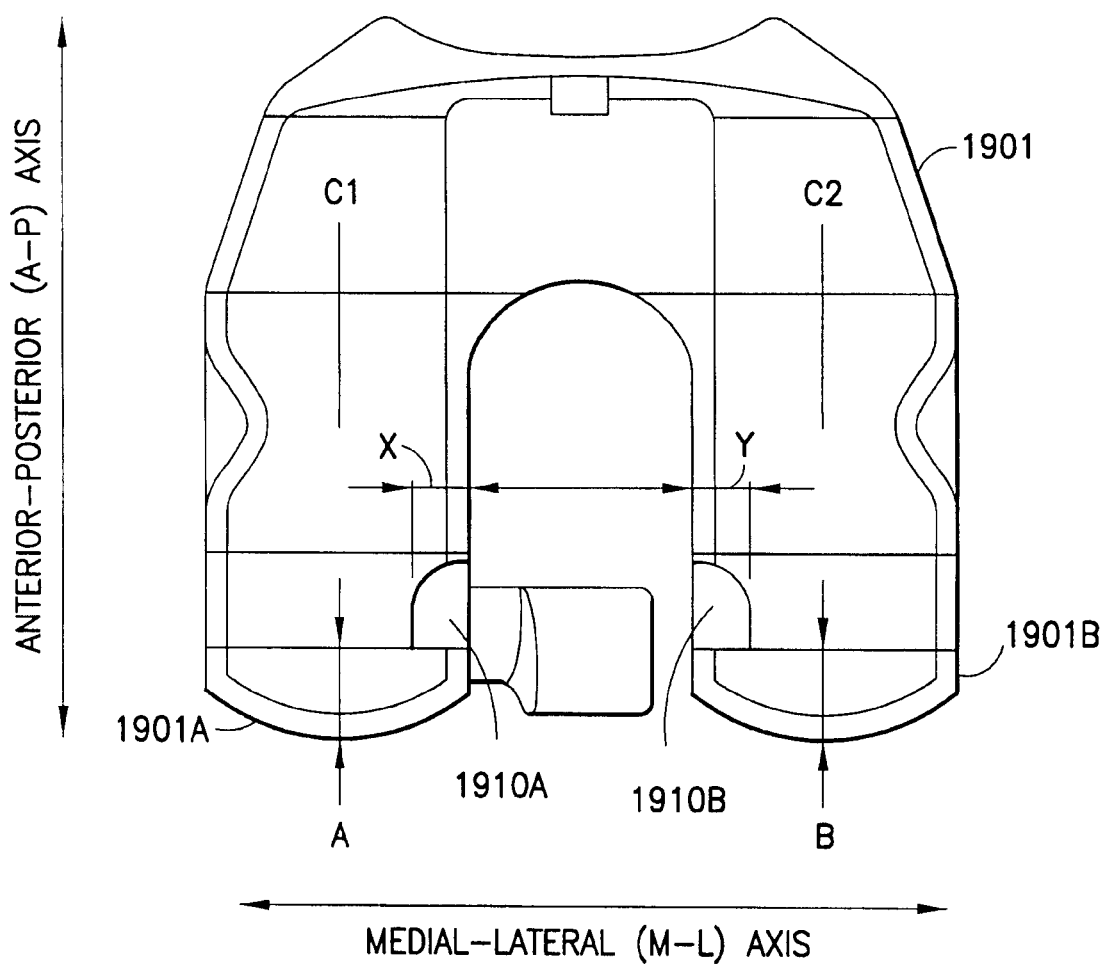
FIG. 19 shows a top view of a femoral component (and modular cam) according to an embodiment of the present invention.

In another example, the first condyle may have an anterior-posterior thickness at a centerline relative to a medial-lateral axis of the first condyle of between about 6 mm and 10 mm (see, e.g., FIG. 19).

In another example, the first condyle may have an anterior-posterior thickness at a centerline relative to a medial-lateral axis of the first condyle of about 8 mm (see, e.g., FIG. 19).

In another example, the prosthesis may further comprise a protector element (see, e.g., 503 of FIG. 5) configured to protect the first attachment mechanism. In another example, the protector element may be removable. In another example, the protector element may protect the integrity of the first attachment mechanism. In another example, the protector element may protect the first attachment mechanism from bone cement and/or soft tissue penetration.

In another embodiment of the present invention a prosthesis (e.g., for implantation in a patient) is provided, comprising: a femoral component (see, e.g., femoral component 1401 of FIGS. 14A-14B or femoral component 1501 of FIGS. 15A-15C), wherein the femoral component comprises a first condyle (see, e.g., condyle 1401A of FIGS. 14A-14B or condyle 1501A of FIGS. 15A-15C) and a second condyle (see, e.g., condyle 1401B of FIGS. 14A-14B or condyle 1501B of FIGS. 15A-15C), wherein the first condyle and the second condyle are disposed apart from one another such that there is a space between the first condyle and the second condyle, wherein the first condyle comprises at least a first surface generally facing the second condyle across the space between the first condyle and the second condyle and wherein the second condyle comprises at least a second surface generally facing the first condyle across the space between the first condyle and the second condyle (see, e.g., FIG. 14A or FIG. 15A); a first attachment mechanism associated with the first surface of the first condyle; a second attachment mechanism associated with the second surface of the second condyle; and a stabilizing mechanism (see, e.g., modular cam 1403 of FIGS. 14A-14B or modular cam 1503 of FIGS. 15A-15C), wherein the stabilizing mechanism comprises a third attachment mechanism (see, e.g., locking pin 1407A of FIG. 14B or locking pin 1505A of FIGS. 15B-15C) and a fourth attachment mechanism (see, e.g., locking pin 1407B of FIG. 14B or locking pin 1505B of FIGS. 15B-15C—in one example, each corresponding first and second attachment mechanism may comprise a receiving hole or the like for each of the aforementioned locking pins); wherein the stabilizing mechanism is attached to the first condyle via a mating between the first attachment mechanism associated with the first surface of the first condyle and the third attachment mechanism of the stabilizing mechanism; wherein the stabilizing mechanism is attached to the second condyle via a mating between the second attachment mechanism associated with the second surface of the second condyle and the fourth attachment mechanism of the stabilizing mechanism; and wherein the stabilizing mechanism is attached to the first condyle and the second condyle from a position in the space between the first condyle and the second condyle (see, e.g., FIGS. 14A and 15A).

In one example, the first condyle may be a left condyle and the second condyle may be a right condyle.

In another example, the first condyle may be a right condyle and the second condyle may be a left condyle.

In another example, each of the first attachment mechanism, second attachment mechanism, third attachment mechanism and fourth attachment mechanism may comprise a portion of a dovetail joint selected from the group consisting of: a female portion of a dovetail joint; and a male portion of a dovetail joint (see, e.g., the dovetail joint shown in FIG. 16B).

In another example, the first attachment mechanism may comprise a first locking pin, the third attachment mechanism may comprise a first hole for receiving the first locking pin, the second attachment mechanism may comprise a second locking pin and the fourth attachment mechanism may comprise a second hole for receiving the second locking pin.

In another example, the first locking pin may be biased towards the first hole by at least a first spring and the second locking pin may be biased towards the second hole by at least a second spring.

In another example, the third attachment mechanism may comprise a first locking pin (see, e.g., locking pin 1407A of FIGS. 14A-14B or locking pin 1505A of FIGS. 15A-15C), the first attachment mechanism may comprise a first hole for receiving the first locking pin, the fourth attachment mechanism may comprise a second locking pin (see, e.g., locking pin 1407B of FIGS. 14A-14B or locking pin 1505B of FIGS. 15A-15C) and the second attachment mechanism may comprise a second hole for receiving the second locking pin.

In another example, the first locking pin may be biased towards the first hole by at least a first spring and the second locking pin may be biased towards the second hole by at least a second spring.

In another example, the first attachment mechanism may be on the first surface of the first condyle.

In another example, the first attachment mechanism may be under the first surface of the first condyle.

In another example, the second attachment mechanism may be on the second surface of the second condyle.

In another example, the second attachment mechanism may be under the second surface of the second condyle.

In another example, the stabilizing mechanism may comprise a cam (see, e.g., modular cam 1403 of FIGS. 14A-14B or modular cam 1503 of FIGS. 15A-15C).

In another example, the stabilizing mechanism may be removably attached to the first condyle and the second condyle.

In another example, the stabilizing mechanism may be essentially permanently attached to the first condyle and the second condyle.

In another example, the stabilizing mechanism may stabilize the femoral component by interfacing with a corresponding feature on a tibial insert adjacent the femoral component see, e.g., FIGS. 12 and 13A-13C).

In another example, the tibial insert may be disposed upon a tibial tray (see, e.g., FIGS. 12 and 13A-13C).

In another example, when the stabilizing mechanism is attached to the first condyle and the second condyle from a position in the space between the first condyle and the second condyle the stabilizing mechanism may be disposed entirely in the space between the first condyle and the second condyle (see, e.g., FIGS. 14A and 15A).

In another example, when the stabilizing mechanism is attached to the first condyle and the second condyle from a position in the space between the first condyle and the second condyle the stabilizing mechanism may be disposed at least partially in the space between the first condyle and the second condyle (see, e.g., FIGS. 14A and 15A).

In another example, the cam may have a cam profile (see, e.g., profile of modular cam 1803 of FIG. 18).

In another example, the cam profile may be in a sagittal plane (see, e.g., profile of modular cam 1803 of FIG. 18).

In another example, the first condyle may have an anterior-posterior thickness at a centerline relative to a medial-lateral axis of the first condyle of between about 6 mm and 10 mm and the second condyle may have an anterior-posterior thickness at a centerline relative to a medial-lateral axis of the second condyle of between about 6 mm and 10 mm (see, e.g., FIG. 19).

In another example, the first condyle may have an anterior-posterior thickness at a centerline relative to a medial-lateral axis of the first condyle of about 8 mm and the second condyle may have an anterior-posterior thickness at a centerline relative to a medial-lateral axis of the second condyle of about 8 mm (see, e.g., FIG. 19).

In another example, the prosthesis may further comprise a first protector element (see, e.g., 503 of FIG. 5) configured to protect the first attachment mechanism and a second protector element (see, e.g., 503 of FIG. 5) configured to protect the second attachment mechanism. In another example, the first protector element may be removable. In another example, the second protector element may be removable. In another example, the first protector element may protect the integrity of the first attachment mechanism. In another example, the second protector element may protect the integrity of the second attachment mechanism. In another example, the first protector element may protect the first attachment mechanism from bone cement and/or soft tissue penetration. In another example, the second protector element may protect the second attachment mechanism from bone cement and/or soft tissue penetration.

Figure 13A:
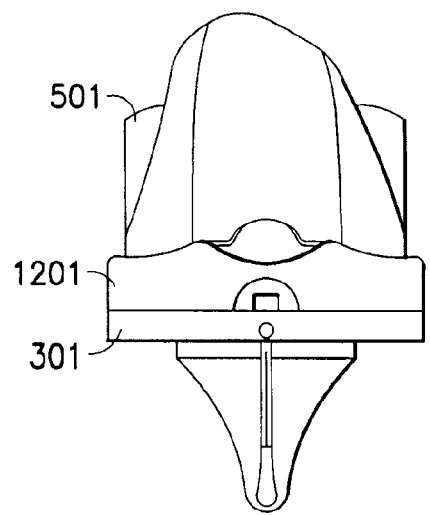
Figure 13B:
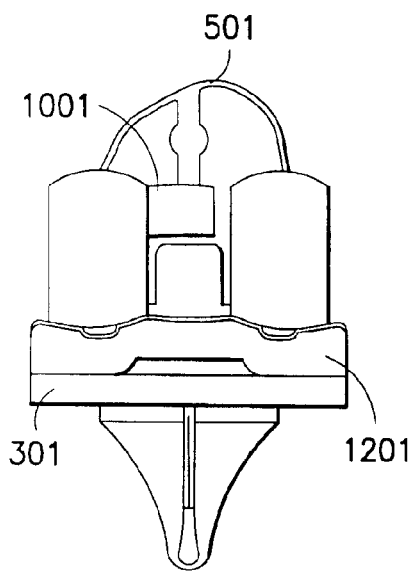
Figure 13C:
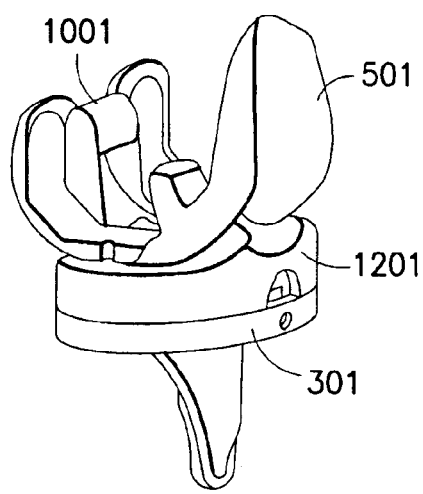

In another embodiment of the present invention a method for modifying a prosthesis implanted in a patient is provided, comprising: implanting a tibial tray (see, e.g., tibial tray 301 of FIGS. 3, 4, 5, 6A-6B, 7, 8, 9, 10, 11, 12 and 13A-13C); installing a cruciate retaining tibial insert on the tibial tray (see, e.g., tibial insert 401 of FIGS. 4, 5, 6A-6B); implanting a cruciate retaining femoral component (see, e.g., femoral component 501 of FIGS. 5, 6A-6B, 7, 8, 9, 10, 11, 12 and 13A-13C); removing the cruciate retaining tibial insert 401; reaming an intercondylar box in bone of the patient (see, e.g., FIG. 10); installing at least one stabilizing mechanism on the implanted cruciate retaining femoral component to convert to a posterior stabilizing femoral component (see, e.g., modular cam 1001 (acting as a stabilizing mechanism) of FIGS. 13A-13C; and installing a posterior stabilizing tibial insert on the tibial tray (see, e.g., tibial insert 1201 of FIGS. 12 and 13A-13C).

In one example, the step of implanting the tibial tray may comprise preparing a tibial bone of the patient to receive the tibial tray.

In another example, the step of implanting the tibial tray may comprise cementing the tibial tray to the tibial bone of the patient (of course, if desired, the tibial tray may be implanted without using cement).

In another example, the step of installing the cruciate retaining tibial insert on the tibial tray may comprise removably locking the cruciate retaining tibial insert to the tibial tray.

In another example, the step of implanting the cruciate retaining femoral component may comprise preparing a femur bone of the patient to receive the cruciate retaining femoral component.

In another example, the step of implanting the cruciate retaining femoral component may comprise cementing the cruciate retaining femoral component to the femur bone of the patient (of course, if desired, the femoral component may be implanted without using cement).

In another example, the step of removing the cruciate retaining tibial insert may comprise removing the cruciate retaining tibial insert without removing the implanted tibial tray.

In another example, the step of removing the cruciate retaining tibial insert may comprise removing the cruciate retaining tibial insert without removing the implanted cruciate retaining femoral component.

In another example, the step of removing the cruciate retaining tibial insert may comprise removing the cruciate retaining tibial insert without removing either of the implanted tibial tray or the implanted cruciate retaining femoral component.

In another example, the steps may be carried out in the order recited.

In another example of an operative technique according to an embodiment of the present invention a tibial tray is not implanted. For example, at the time of the trial reduction, the surgeon will decide if CR or PS components need to be implanted. If PS is needed, then the surgeon will attach the modular cam to the femoral component at that time, outside the patient's body (e.g., on the back table).

In another example, various embodiments of the present invention may provide for a reduction in required inventory. In this regard, it is believed that a hospital typically handles full inventory of left and right CR femoral components and left and right PS femoral components. Under various embodiments of the present invention, only the left and right CR femoral components and the corresponding modular cam(s) are needed to perform surgeries for both CR and PS type indications (for example, in the case of CR indication, a CR femoral component would be used, while in the case of PS indication, a modular cam would be mounted on a CR femoral component to convert the CR femoral component to a PS femoral component).

In another embodiment of the present invention significant resection of the posterior femur may not be required.

In another embodiment of the present invention insertion of the modular cam may not need to be done from the side of the femoral component—an area typically quite difficult to access during surgery.

In another embodiment of the present invention the cam profile may provide beneficial kinematics.

In another embodiment of the present invention the prosthesis may be a meniscal bearing knee prosthesis.

In another embodiment of the present invention the prosthesis may be a knee prosthesis other than a meniscal bearing knee prosthesis.

In another embodiment of the present invention the modular cam may be mounted in a non-reversible manner.

In another embodiment of the present invention the surgeon may not need to prepare a large intercondylar box cut at the time of the primary surgery in case a revision is necessary later.

In another embodiment of the present invention the exchange of the original cruciate-retaining type tibial insert for a posterior-stabilizing type tibial insert in the event of revision may be provided (that is, one of the components may be explanted).

In another embodiment of the present invention a smooth conversion from a CR knee system to a PS knee system may be provided.

In another embodiment of the present invention the CR knee system may not compromise function in order to prepare for the remote possibility of revision.

In another embodiment of the present invention the bone cuts required may preserve as much patient bone as possible.

In another embodiment of the present invention in event of a revision surgery, the conversion may be simple.

As described herein, various embodiments of the present invention provide for converting a CR knee system into a PS knee system without removing the tibial baseplate and femoral component from the patient.

Further, as described herein, various embodiments of the present invention provide a CR femoral component that can receive a modular cam, and as a result be converted to a PS femoral component.

Further, as described herein, various embodiments of the present invention provide for converting a CR knee to PS knee without exchanging certain components (e.g., those components affixed to bone).

Further, as described herein, various embodiments of the present invention provide for having a modular cam attached to only one condyle.

Further, as described herein, various embodiments of the present invention provide for having a modular cam attached to both condyles.

Further, as described herein, various embodiments of the present invention provide for having a protector (e.g., made from plastic) to protect the locking mechanism(s) located on the femoral component from soft tissue and/or bone cement intrusion, when a modular cam is not used.

Further, as described herein, various embodiments of the present invention provide for revision of the femoral component in case of PCL deficiency.

In another embodiment of the present invention a surgical method is provided, comprising: implanting a tibial tray; installing a cruciate retaining tibial insert on the tibial tray; implanting a cruciate retaining femoral component; removing the cruciate retaining tibial insert; reaming the intercondylar box (i.e., bone); installing at least one stabilizing mechanism (e.g., modular cam) on the implanted cruciate retaining femoral component to convert to a posterior stabilizing femoral component; installing a posterior stabilizing tibial insert on the tibial tray.

In another embodiment of the present invention a stabilizing mechanism (e.g., modular cam) is installed on a femoral component by being attached to the femoral component from a location between the two condyles—see, e.g., FIGS. 14A-14B, 15A-15C and 16A-16F regarding this location between the condyles (this location contrasts with a location at an outer position of the condyles—that is, from a side of one condyle furthest away from the other condyle). In one example, the stabilizing mechanism is attached to one condyle; in another example, the stabilizing mechanism is attached to both condyles (e.g., bridging the condyles).

In another embodiment of the present invention a femoral component may be provided that does not require at its initial implantation the cutting from bone of a box or the like that may not be used.

In another embodiment of the present invention a modular cam element may be mounted to a femoral component in an intracondylar manner (as opposed, for example, to being mounted through the condyles from one outer side or the other). In one specific example, a modular cam element may be mounted to a femoral component at an inside area of one condyle of the femoral component. In another specific example, a modular cam element may be mounted to a femoral component at inside areas of two condyles (e.g., left and right) of the femoral component.

Figure 17:
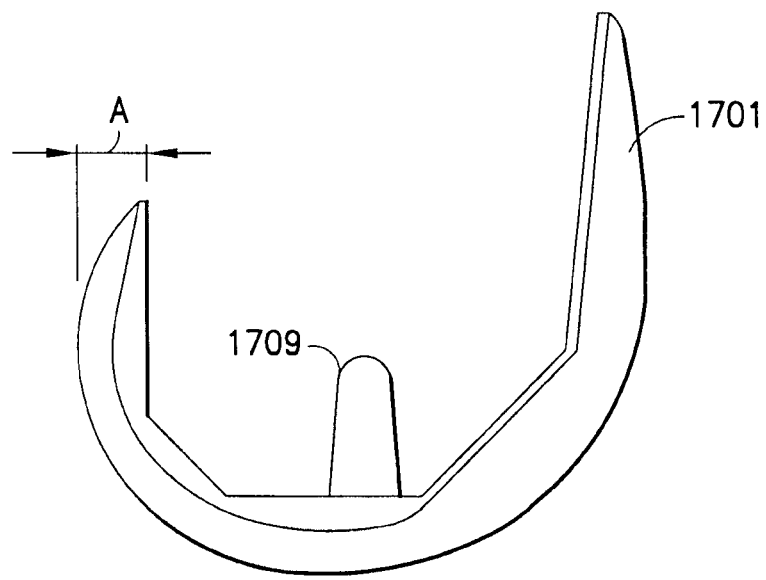
FIG. 17 shows a side view of a femoral component according to an embodiment of the present invention.

Referring now to FIG. 17, this FIG. shows a side view of a femoral component 1701 according to an embodiment of the present invention (in this example, femoral component 1701 includes peg 1709 (e.g., on a distal surface), for example, to aid in stabilization; in another example, the femoral component may not utilize such a peg—rather stabilization may be aided by condyle "bumps" discussed further below. In another example, both a peg and condyle "bumps" may be provided.

Of note, the concept of attaching a modular component (e.g., modular cam) between the two femoral condyles enables (in this example) maintaining a relatively small thickness of the posterior condyles (for example, at the centerline (relative to the M-L axis) of each of the condyles—see, e.g., centerline C1 and centerline C2 shown in FIG. 19). In one example, the thickness (see, e.g., dimension A along the A-P axis in FIG. 17 and dimensions A and B along the A-P axis in FIG. 19—in one example, dimensions A and B may be essentially the same) may be in the range of between about 6 mm-10 mm. In a more specific example, the thickness (see, e.g., dimension A along the A-P axis in FIG. 17 and dimensions A and B along the A-P axis in FIG. 19—in one example, dimensions A and B may be essentially the same) may be about 8 mm. In this regard, thinner posterior condyles may minimize bone removal.

Referring now to FIG. 18, this FIG. shows a side cross-section view of a femoral component 1801 (and modular cam 1803) according to an embodiment of the present invention.

As seen, in one example, the modular element (e.g., modular cam) may feature a desired cam profile (e.g., non-circular in cross-section) in order to interact with the spine of the tibial insert (in one example, the modular element may comprise a cam profile in order to achieve an optimum rollback in flexion). In another example, the cam profile may be in a sagittal plane. In another example, the modular element is not (in this example) assembled by screwing, enabling the modular element to be accurately placed and orientated (see, e.g., FIG. 18).

Referring now once again to FIG. 19, it is seen that condyle 1901A may include "bump" 1910A (extending dimension X in the M-L axis) and that condyle 1901B may include "bump" 1910B (extending dimension Y in the M-L axis). In one example, X and Y may be essentially the same. In another example, such "bumps" 1910A,1910B provided on the femoral component 1901 may be sufficiently designed to stabilize the femoral component (e.g., along the M-L axis), In another example, such "bumps" 1910A,1910B provided on the femoral component 1901 may be sufficiently designed to stabilize the femoral component (e.g., along the M-L axis) such that a peg (see, e.g., peg 1709 of FIG. 17) may not be required.

Figure 20:
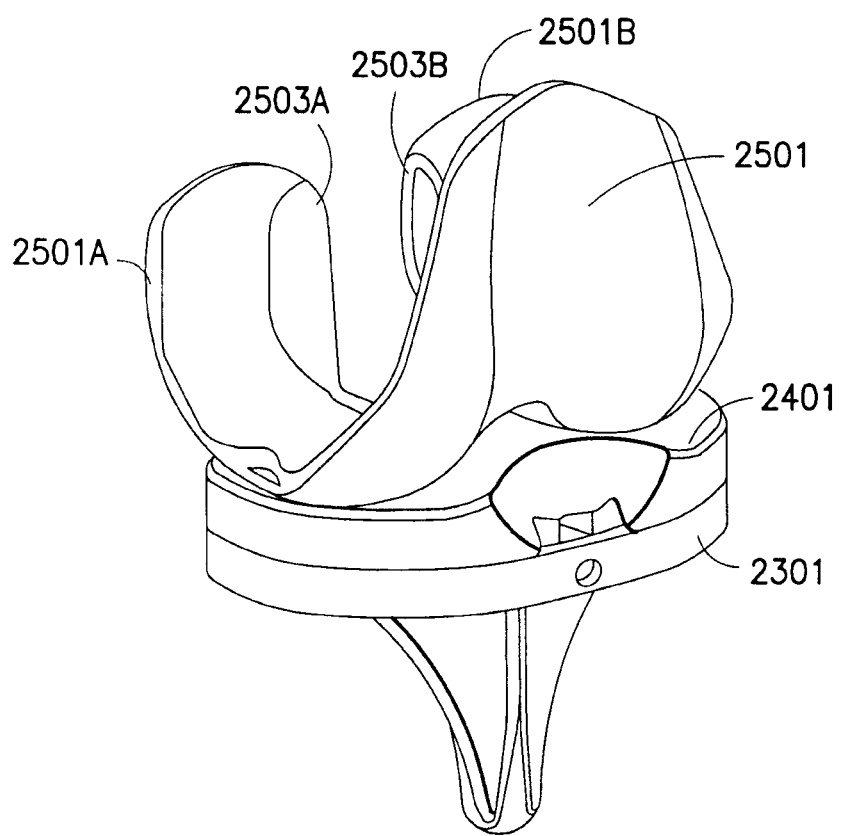
FIG. 20 shows a view of another embodiment of the present invention.

Referring now to FIG. 20, another view of condyle "bumps" according to an embodiment of the present invention are shown. More particularly, it is seen that this FIG. shows tibial tray 2301, tibial insert 2401 and femoral component 2501 (including condyle 2501A, condyle "bump" 2503A, condyle 2501B and condyle "bump" 2503B). As mentioned above, in one example, such "bumps" provided on the femoral component may be sufficiently designed to stabilize the femoral component (e.g., along the M-L axis). In another example, such "bumps" provided on the femoral component may be sufficiently designed to stabilize the femoral component (e.g., along the M-L axis) such that a peg (see, e.g., peg 1709 of FIG. 17) may not be required.

In another example, a modular cam may be releasably locked or attached to one or more condyles of the femoral component.

In another example, a modular cam may be essentially permanently locked or attached to one or more condyles of the femoral component (wherein "permanently" refers to being locked or attached in such a manner that non-destructive removal would be difficult or impossible).

In another example, one or more components may be packaged in one or more kits (e.g., one type of kit with a CR femoral component, CR tibial insert and a tibial tray and another type of kit with a modular cam (for converting a CR femoral component into a PS femoral component) and a PS tibial insert).

In another example, the stabilizing mechanism (e.g., modular cam) may be attached to the femoral component from any desired direction (e.g., from the top of the femoral component, from the bottom of the femoral component, from the front of the femoral component or from the back of the femoral component).

Of course, any embodiment/example described herein (or any feature or features of any embodiment/example described herein) may be combined with any other embodiment/example described herein (or any feature or features of any such other embodiment/example described herein).

While a number of embodiments/examples of the present invention have been described, it is understood that these embodiments/examples are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone ingrowth or prohibit surface bone ingrowth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof. Further still, any metal construct may be a machined metal construct. Further still, any number of protrusions (e.g., such as for initial fixation by forming a bond with cement and/or such as for supplemental fixation by forming a bond with cement) may be utilized with a given prosthesis. Further still, any number of female features that increase the cement mantle may be utilized with a given prosthesis. Further still, any number of male features that could dig into the bone so that initial/supplemental fixation can be improved may be utilized with a given prosthesis. Further still, any number of bone screws (e.g., such as for initial fixation and/or such as for supplemental fixation) may be utilized with a given prosthesis. Further still, any components described herein may be combined with any other components described herein. Further still, any steps described herein may be carried out in any desired order (and any additional steps may be added as desired and/or any steps may be deleted as desired).

What is claimed is:

1. A prosthesis, comprising:
    a femoral component,
        wherein the femoral component comprises a first condyle and a second condyle, wherein the first condyle and the second condyle are disposed apart from one another such that there is a space between the first condyle and the second condyle,
        wherein the first condyle comprises at least a first surface generally facing the second condyle across the space between the first condyle and the second condyle and wherein the second condyle comprises at least a second surface generally facing the first condyle across the space between the first condyle and the second condyle;
    a first attachment mechanism associated with the first surface of the first condyle;
    a second attachment mechanism associated with the second surface of the second condyle; and
    a modular stabilizing mechanism,
        wherein the modular stabilizing mechanism comprises a third attachment mechanism and a fourth attachment mechanism;
    wherein the modular stabilizing mechanism is configured to permanently attach in a non-reversible manner to the first condyle of the femoral component via a mating between the first attachment mechanism associated with the first surface of the first condyle and the third attachment mechanism of the modular stabilizing mechanism;
    wherein the modular stabilizing mechanism is configured to permanently attach in a non-reversible manner to the second condyle of the femoral component via a mating between the second attachment mechanism associated with the second surface of the second condyle and the fourth attachment mechanism of the modular stabilizing mechanism; and
    wherein the modular stabilizing mechanism is attached to the first condyle and the second condyle of the femoral component from a position in the space between the first condyle and the second condyle.

2. The prosthesis of claim 1, wherein the first attachment mechanism comprises a first locking pin, the third attachment mechanism comprises a first hole for receiving the first locking pin, the second attachment mechanism comprises a second locking pin and the fourth attachment mechanism comprises a second hole for receiving the second locking pin.

3. The prosthesis of claim 2, wherein the first locking pin is biased towards the first hole by at least a first spring and the second locking pin is biased towards the second hole by at least a second spring.

4. The prosthesis of claim 1, wherein the third attachment mechanism comprises a first locking pin, the first attachment mechanism comprises a first hole for receiving the first locking pin, the fourth attachment mechanism comprises a second locking pin and the second attachment mechanism comprises a second hole for receiving the second locking pin.

5. The prosthesis of claim 4, wherein the first locking pin is biased towards the first hole by at least a first spring and the second locking pin is biased towards the second hole by at least a second spring.

6. The prosthesis of claim 1, wherein the first attachment mechanism is on the first surface of the first condyle.

7. The prosthesis of claim 1, wherein the second attachment mechanism is on the second surface of the second condyle.

8. The prosthesis of claim 1, wherein the modular stabilizing mechanism comprises a cam.

9. The prosthesis of claim 1, wherein the modular stabilizing mechanism stabilizes the femoral component by interfacing with a corresponding feature on a tibial insert adjacent the femoral component.

10. The prosthesis of claim 9, wherein the tibial insert is disposed upon a tibial tray.

11. The prosthesis of claim 1, wherein when the modular stabilizing mechanism is attached to the first condyle and the second condyle from a position in the space between the first condyle and the second condyle the modular stabilizing mechanism is disposed entirely in the space between the first condyle and the second condyle.

12. The prosthesis of claim 1, wherein when the modular stabilizing mechanism is attached to the first condyle and the second condyle from a position in the space between the first condyle and the second condyle the modular stabilizing mechanism is disposed at least partially in the space between the first condyle and the second condyle.

13. The prosthesis of claim 8, wherein the cam has a cam profile.

14. The prosthesis of claim 13, wherein the cam profile is in a sagittal plane.

15. The prosthesis of claim 1, wherein the first condyle has an anterior-posterior thickness at a centerline relative to a medial-lateral axis of the first condyle of between about 6 mm and 10 mm and wherein the second condyle has an anterior-posterior thickness at a centerline relative to a medial-lateral axis of the second condyle of between about 6 mm and 10 mm.

16. The prosthesis of claim 15, wherein the first condyle has an anterior-posterior thickness at a centerline relative to a medial-lateral axis of the first condyle of about 8 mm and wherein the second condyle has an anterior-posterior thickness at a centerline relative to a medial-lateral axis of the second condyle of about 8 mm.

* * * * *

UNITED STATES PATENT AND TRADEMARK OFFICE
CERTIFICATE OF CORRECTION

| | |
|---|---|
| PATENT NO. | : 8,506,640 B2 |
| APPLICATION NO. | : 12/558238 |
| DATED | : August 13, 2013 |
| INVENTOR(S) | : Laurent Angibaud et al. |

Page 1 of 1

It is certified that error appears in the above-identified patent and that said Letters Patent is hereby corrected as shown below:

On the Title Page, Item (54) and in the Specification, Col. 1, Line 5, in the title, Delete "STABILIZNG" and insert -- STABILIZING --.

Signed and Sealed this
Twenty-first Day of October, 2014

Michelle K. Lee
*Deputy Director of the United States Patent and Trademark Office*